United States Patent [19]
Nikoonahad et al.

[11] Patent Number: 6,108,087
[45] Date of Patent: Aug. 22, 2000

[54] NON-CONTACT SYSTEM FOR MEASURING FILM THICKNESS

[75] Inventors: Mehrdad Nikoonahad, Menlo Park; Shing Lee; Haiming Wang, both of Fremont, all of Calif.

[73] Assignee: Kla-Tencor Corporation, San Jose, Calif.

[21] Appl. No.: 09/028,417

[22] Filed: Feb. 24, 1998

[51] Int. Cl.[7] .................................................. G01B 9/02
[52] U.S. Cl. ..................................... 356/359; 356/432 T
[58] Field of Search ..................................... 356/357, 359, 356/358, 432 T, 73, 655, 657, 347, 35.5

[56] References Cited

U.S. PATENT DOCUMENTS

| | | |
|---|---|---|
| 3,978,713 | 9/1976 | Penney . |
| 4,379,633 | 4/1983 | Bickel et al. ............................ 356/359 |
| 4,522,510 | 6/1985 | Rosencwaig et al. . |
| 4,541,280 | 9/1985 | Cielo et al. . |
| 4,579,463 | 4/1986 | Rosencwaig et al. . |
| 4,619,529 | 10/1986 | Iuchi et al. ............................... 356/358 |
| 4,636,088 | 1/1987 | Rosencwaig et al. . |
| 4,679,946 | 7/1987 | Rosencwaig et al. . |
| 4,710,030 | 12/1987 | Tauc et al. . |
| 4,752,140 | 6/1988 | Cielo et al. . |
| 5,294,289 | 3/1994 | Heinz et al. . |
| 5,479,259 | 12/1995 | Nakata et al. . |
| 5,585,921 | 12/1996 | Pepper et al. . |
| 5,604,592 | 2/1997 | Kotidiis et al. .......................... 356/357 |
| 5,619,326 | 4/1997 | Takamatsu et al. . |
| 5,623,307 | 4/1997 | Kotidis et al. . |
| 5,672,830 | 9/1997 | Rogers et al. . |

FOREIGN PATENT DOCUMENTS 0702230   3/1996   European Pat. Off. .

OTHER PUBLICATIONS

Written Opinion mailed Jan. 11, 2000.

Primary Examiner—Robert H. Kim
Assistant Examiner—Andrew H. Lee
Attorney, Agent, or Firm—Majestic, Parsons, Siebert & Hsue P.C.

[57] ABSTRACT

Thickness of a film in a sample may be detected by directing pump laser pulses to the surface of a sample to generate an acoustic pulse in a sample. The acoustic pulse propagates downwards until it reaches an interface between the bottom of the film and a substrate and is reflected back to the top surface of the film as a first echo. A reflection of the first echo propagates downwards and is again reflected back towards the surface as a second echo. Interferometry is used to measure the lapse of time between the first and second echos from which the thickness of the film may be determined.

114 Claims, 12 Drawing Sheets

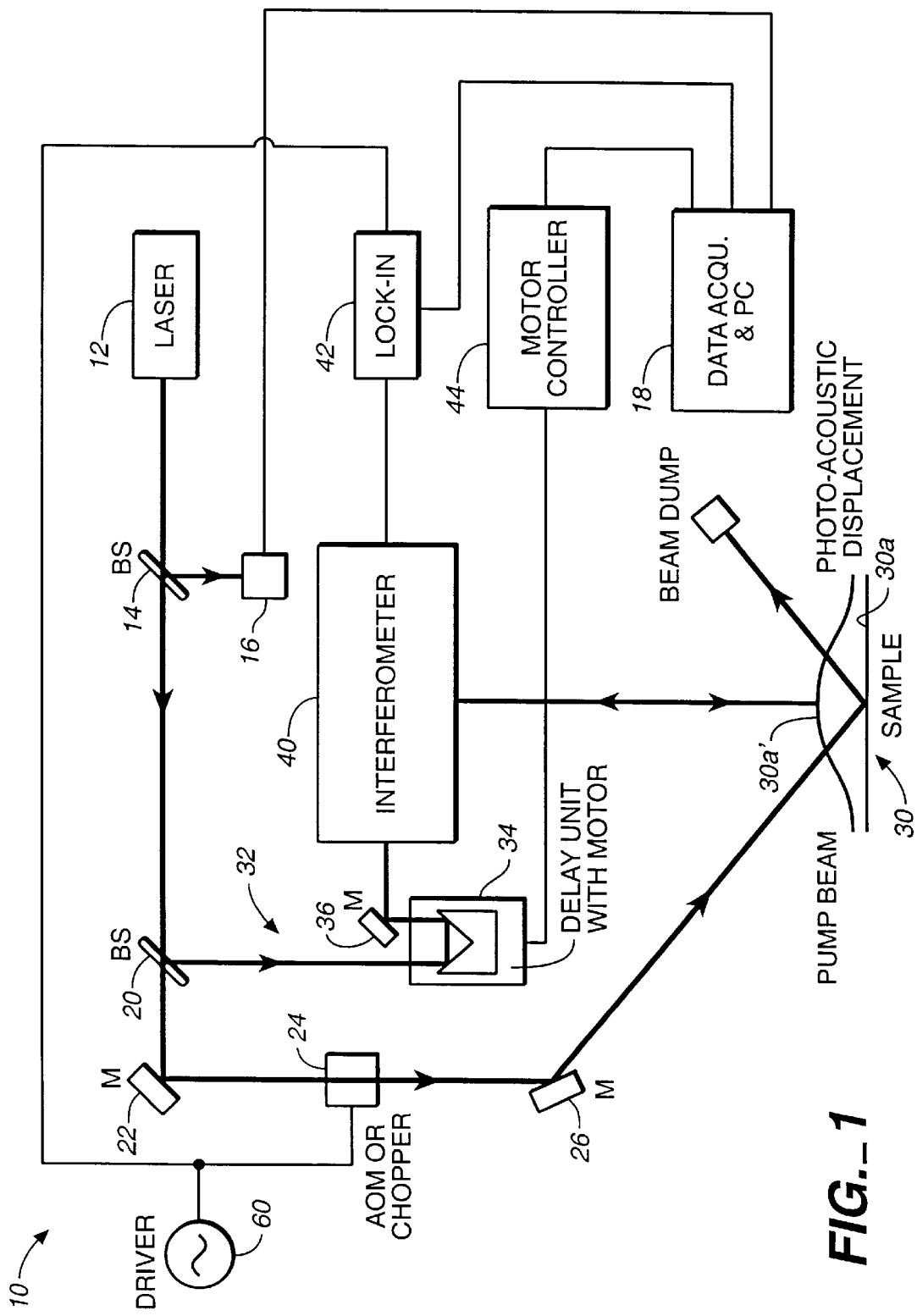
FIG._1

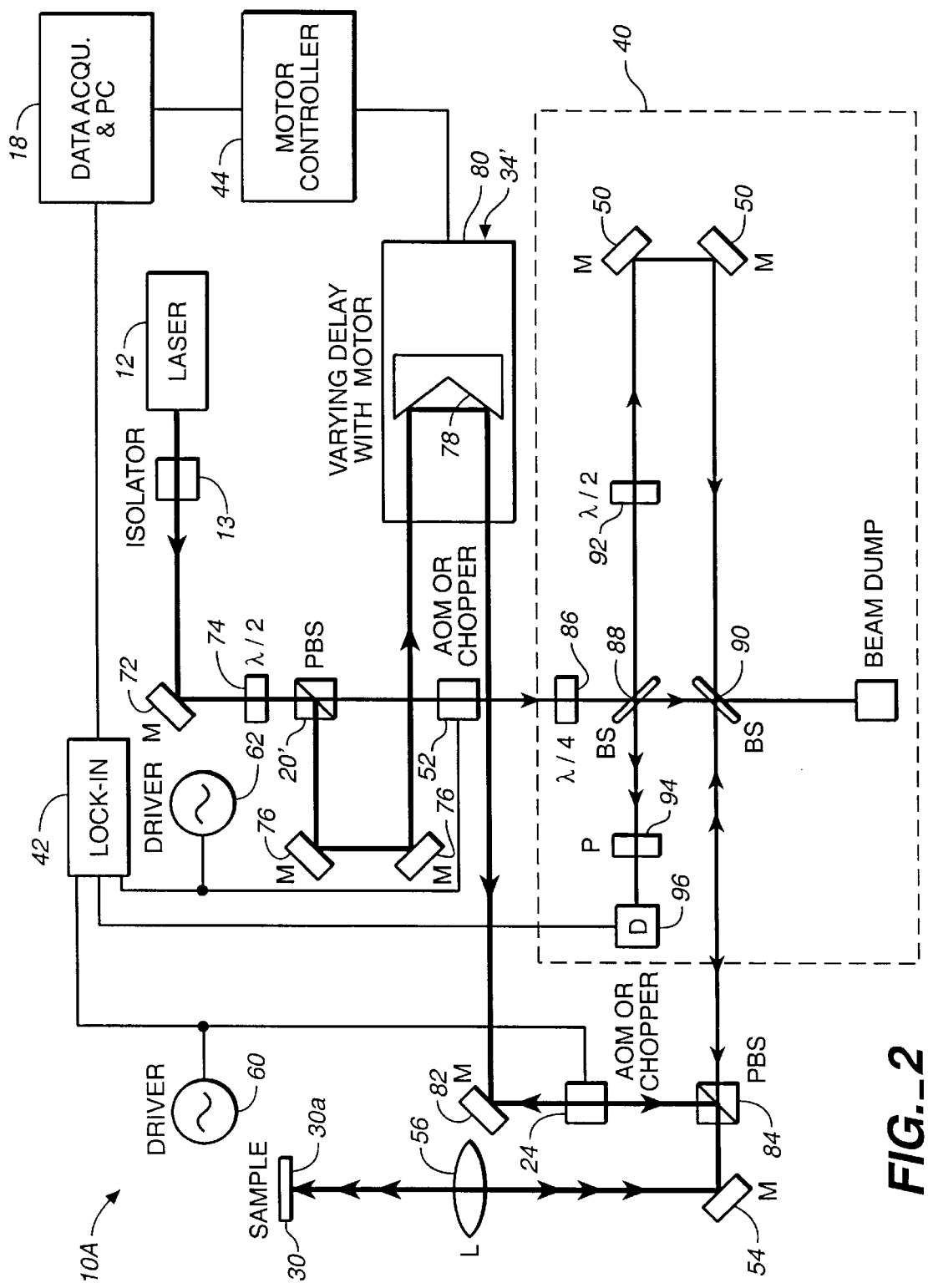
FIG._2

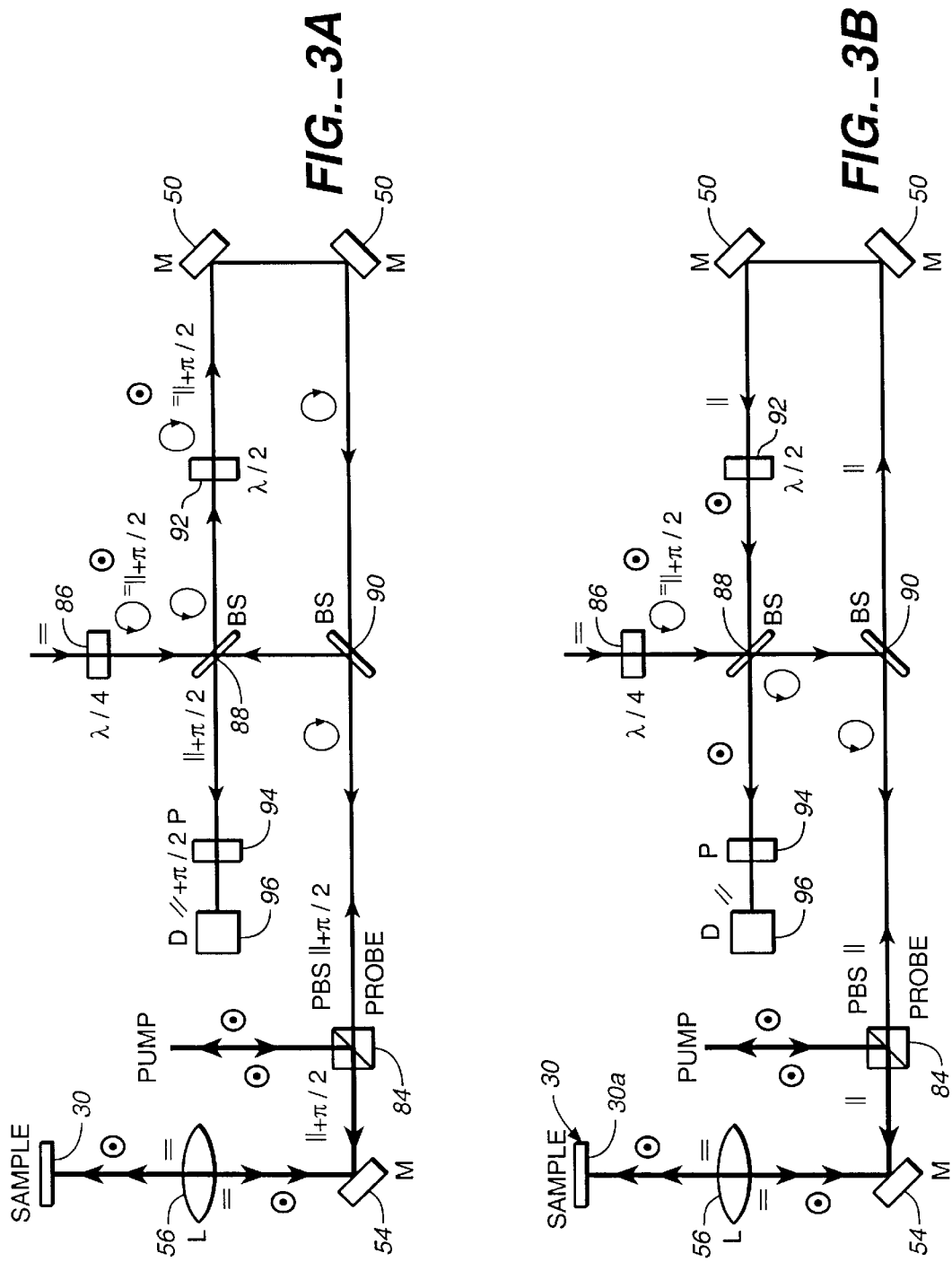

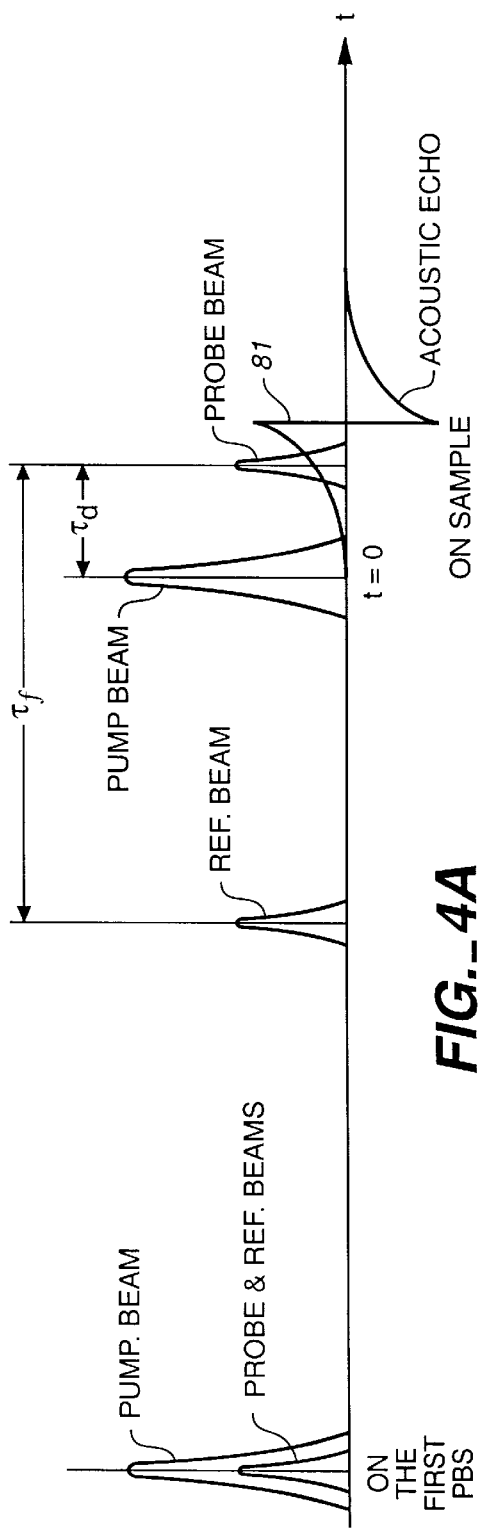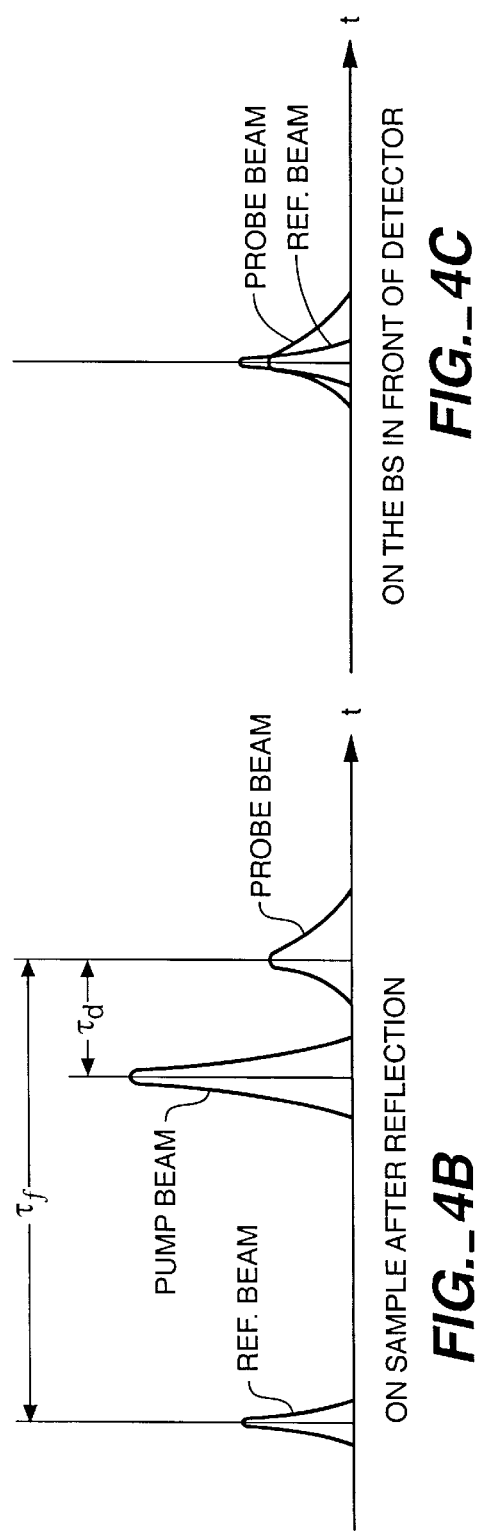

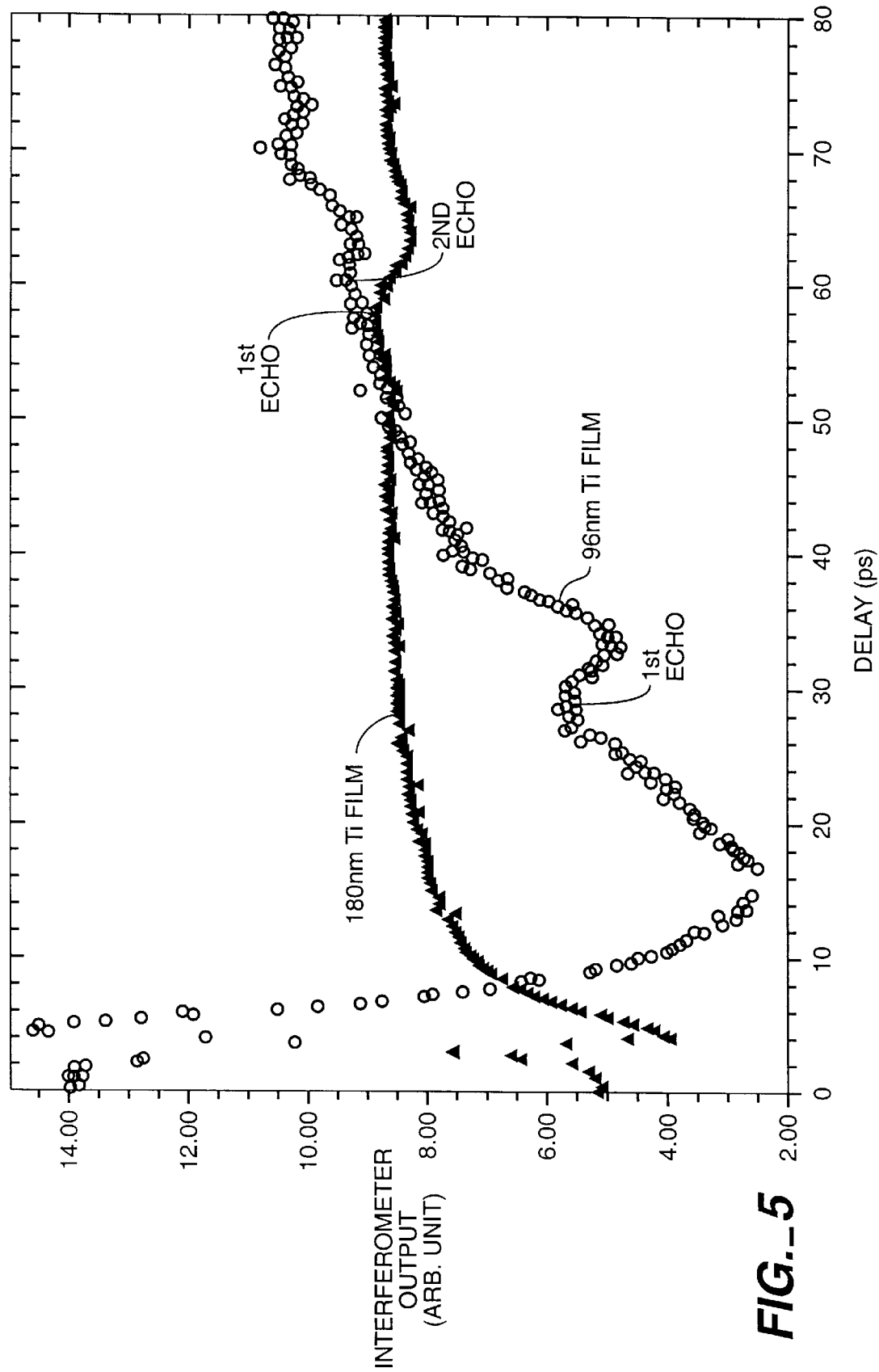
FIG._5

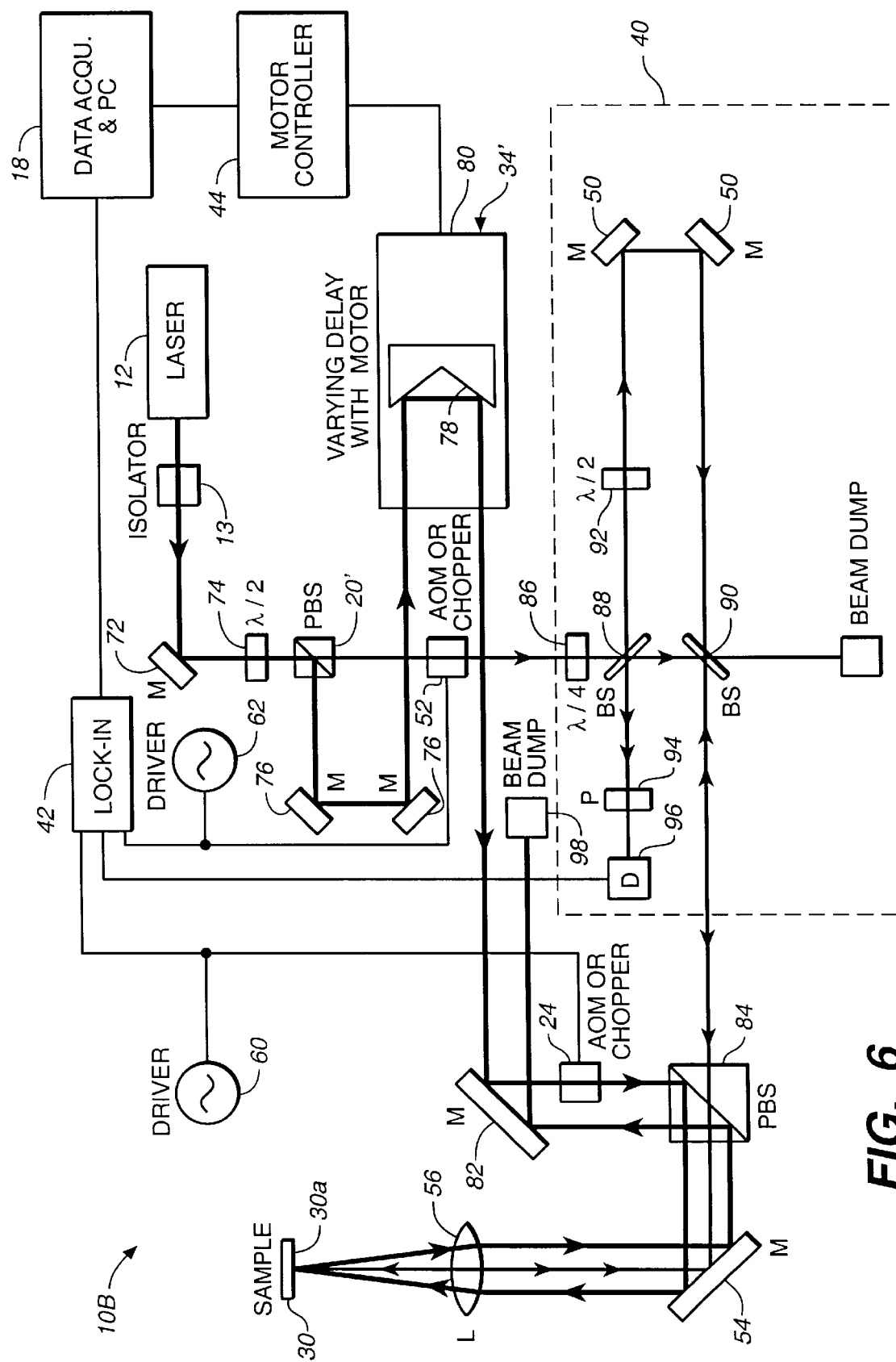
FIG._6

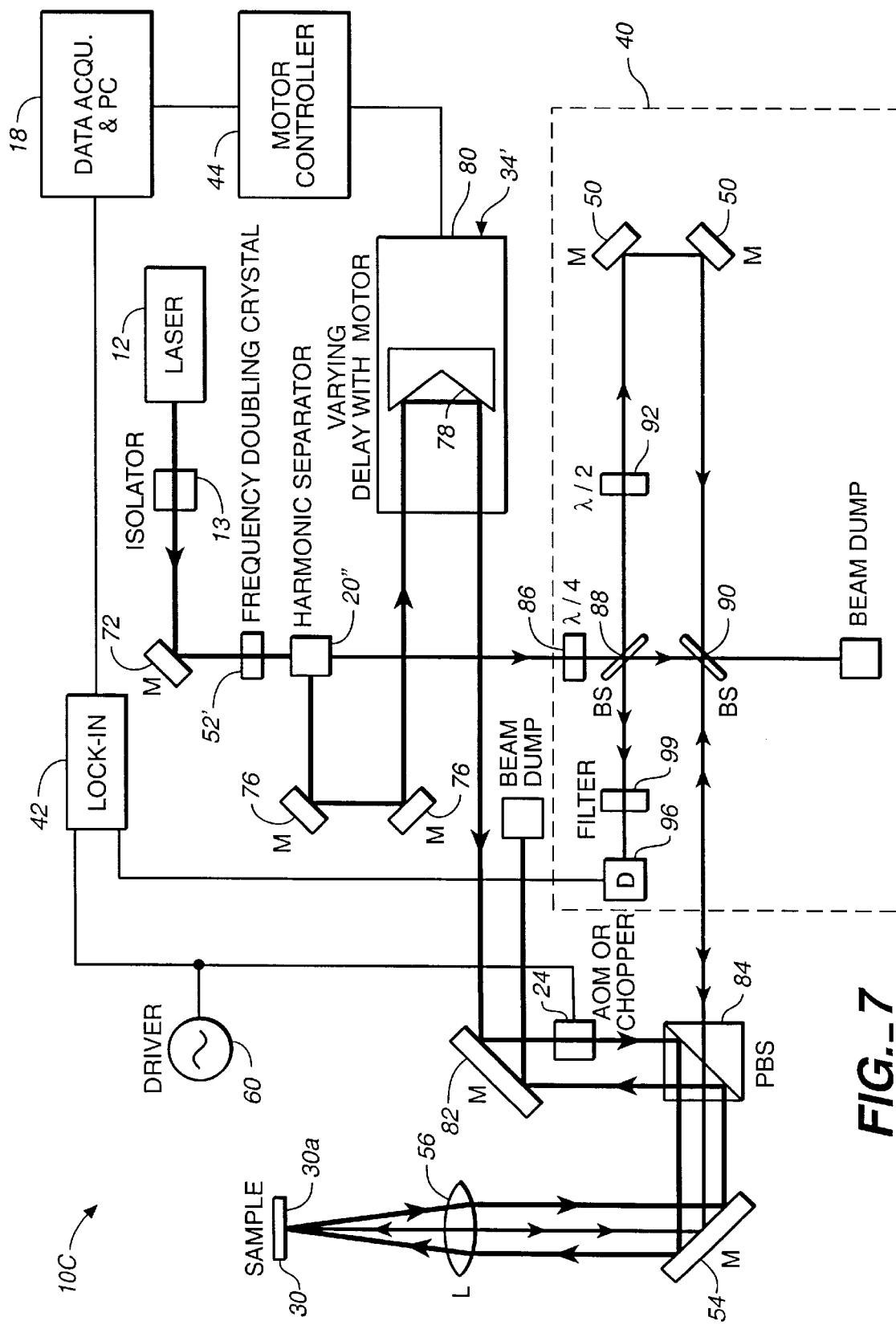
FIG._7

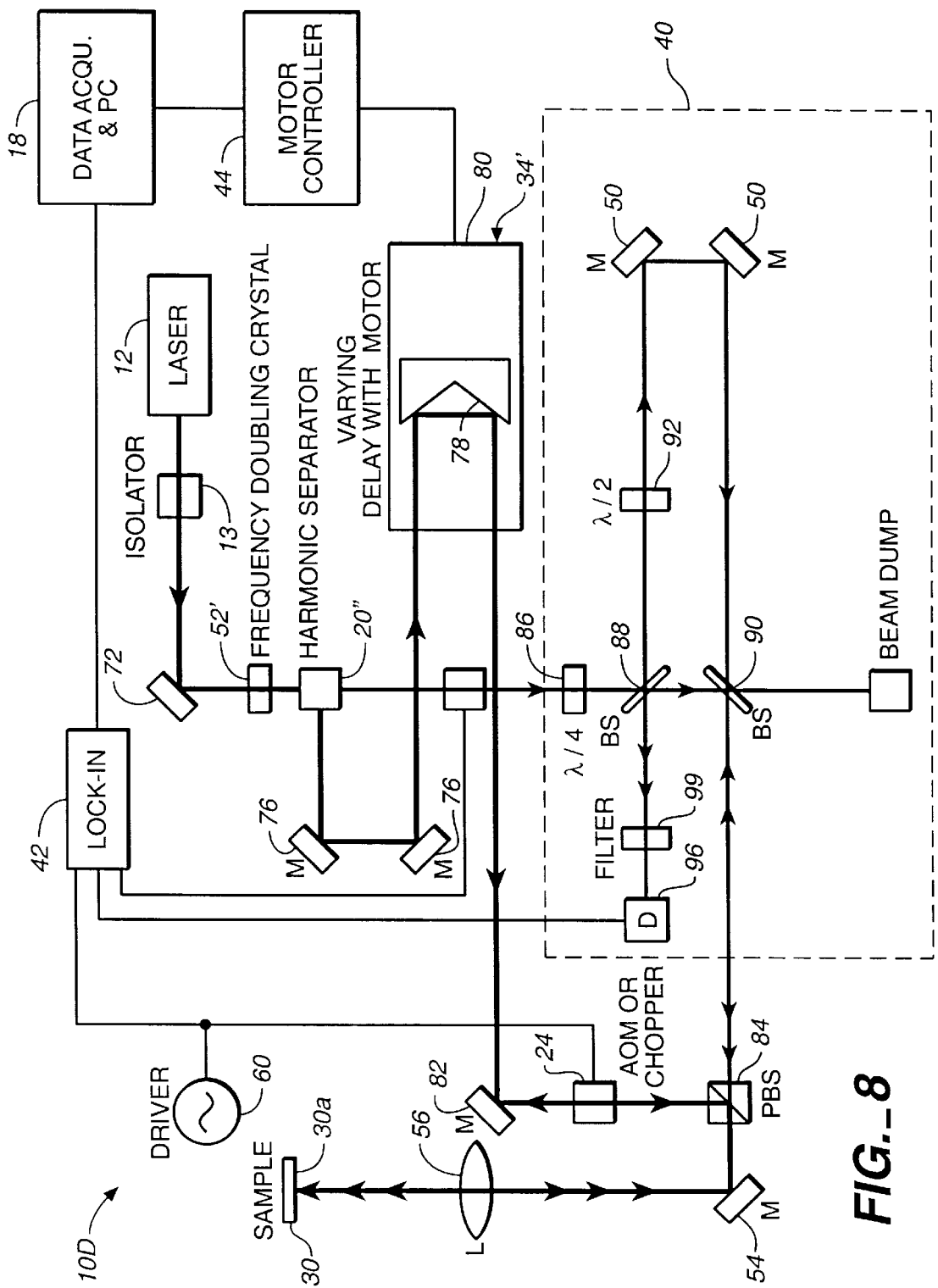
FIG._8

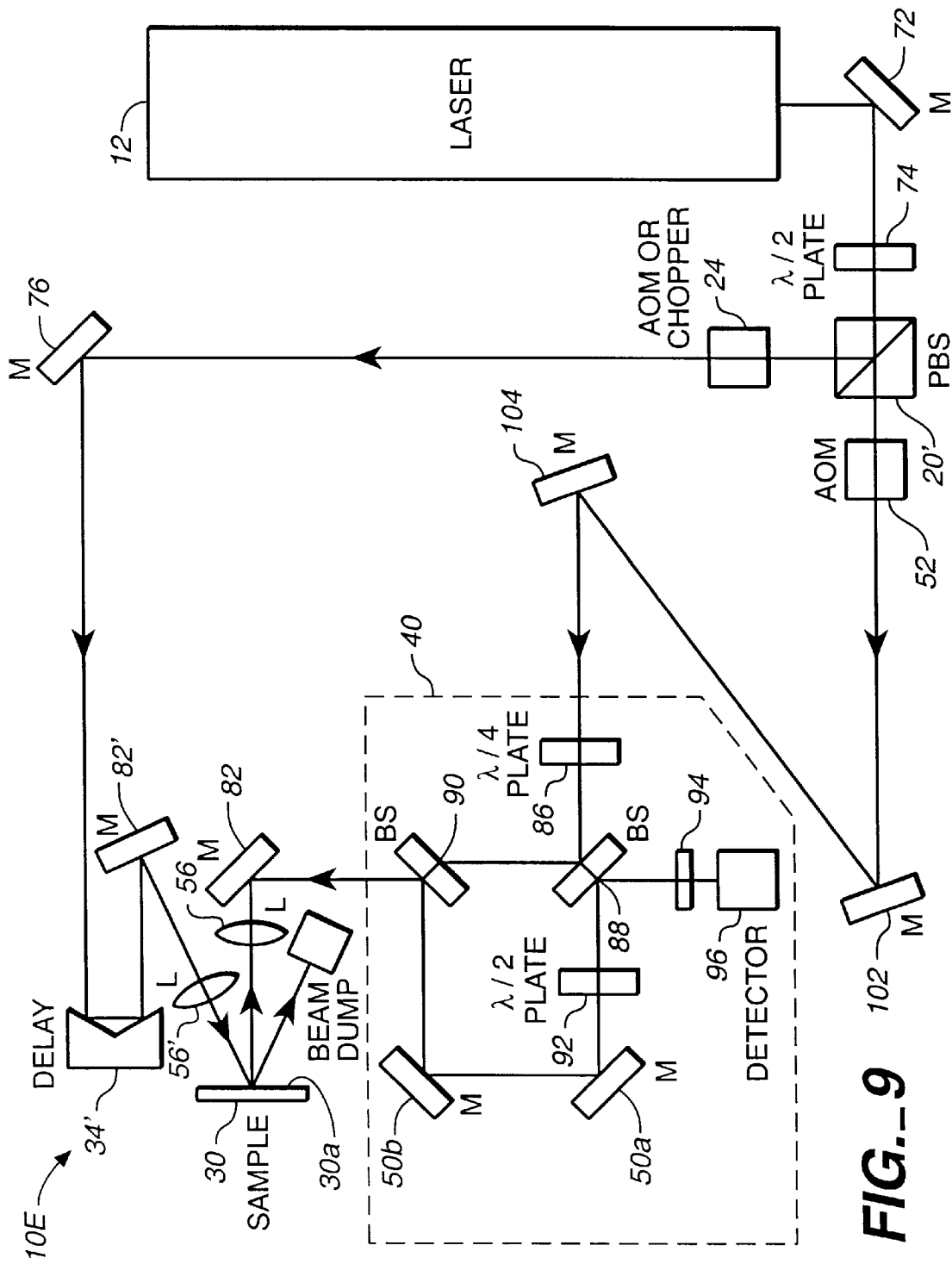
FIG._9

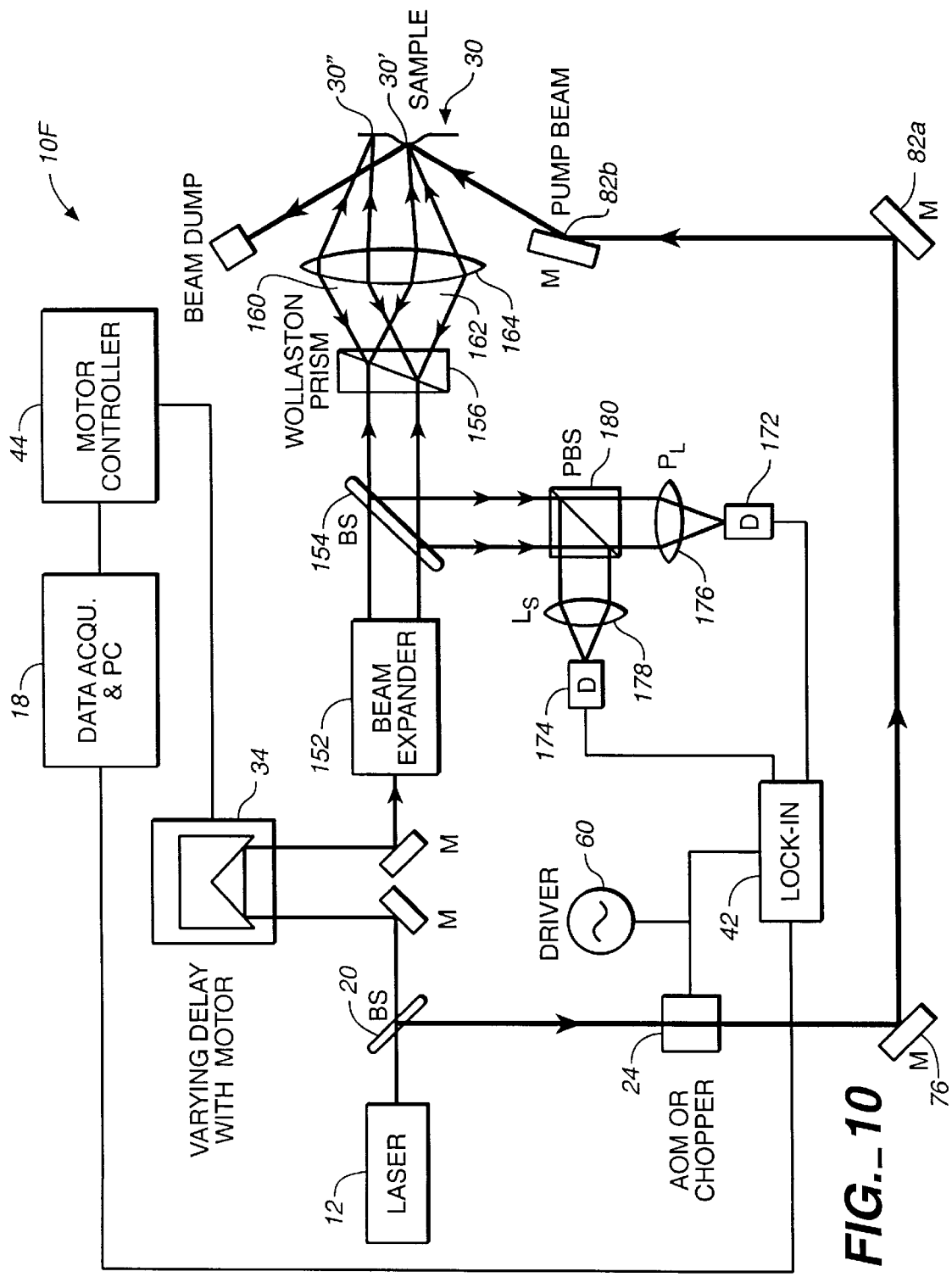
FIG._10

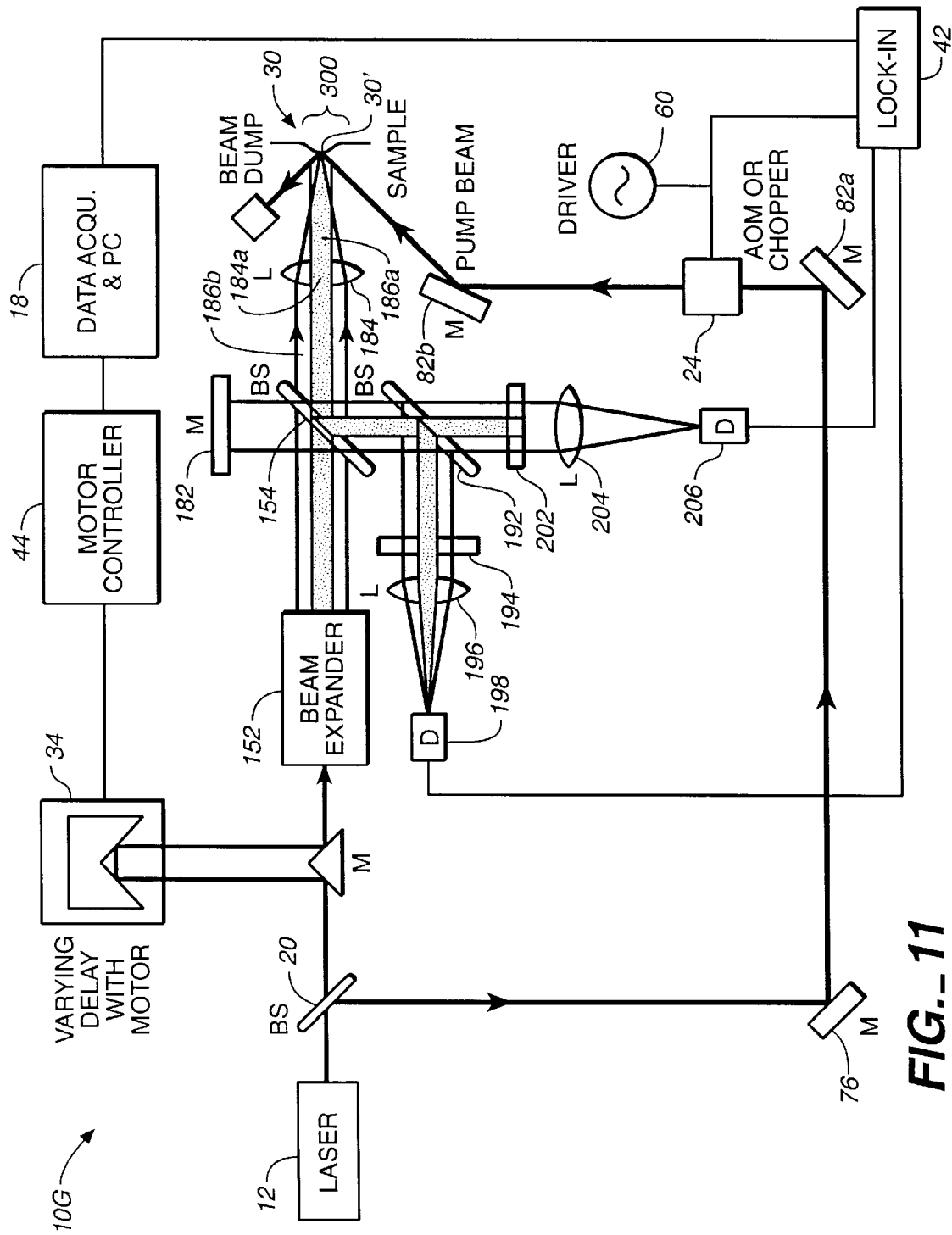
FIG._11

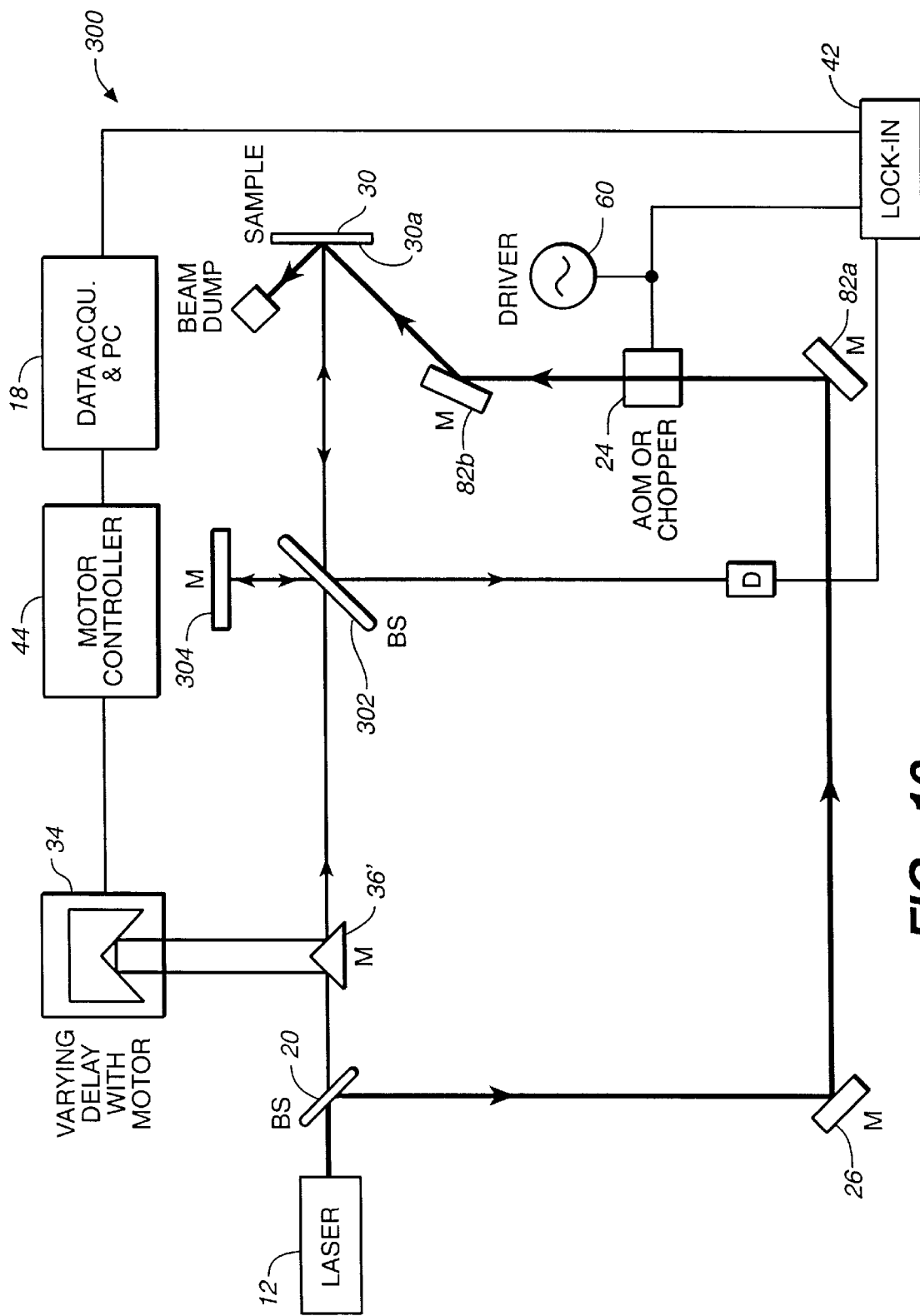
FIG._12

NON-CONTACT SYSTEM FOR MEASURING FILM THICKNESS

BACKGROUND OF THE INVENTION

This invention relates in general to thickness measurement of structures and, in particular, to a system for measuring film thickness through laser induced acoustic pulse-echo using non-contact interferometry.

Ellipsometry is a powerful technique for film thickness measurement in semiconductor processing. In cases where the film under examination is transparent to the illuminating radiation, ellipsometry can measure films down to one monolayer thick (3–10 Angstroms). However, ellipsometry fails in cases where the film under examination is opaque. Metallic films, which play a major role in integrated circuit fabrication, fall into this category. Optical radiation is absorbed within the first few tens to hundreds of Angstroms of the film, depending on the wavelength and material under examination. For example, using green radiation at a wavelength of 0.5 micron in aluminum, the absorption length is less than 70 Angstroms. At longer wavelengths, and in particular at infra-red wavelengths, this situation gets better, but still ellipsometry cannot provide the full solution with reference to metallic films or other optically opaque films.

Time resolved pulse-echo ultrasound is a well known technique for thickness measurement in situations where the thickness of interest is a few millimeters or at least tens of microns. For films used in semiconductor processing, one needs extremely short pulses so that the surface echo can be time resolved. Such pulses can be generated by short laser pulses and the general area of this art is known as photoacoustics. The physical processes involved is as follows: a short laser pulse is absorbed within one absorption length from the surface, causing a rise in local temperature of the surface. Through the temperature coefficient of expansion (expansivity) the film undergoes thermal stresses leading to an elastic pulse which propagates across the film at the speed of sound. Given the velocity of sound in the film, if one measures the time of flight across the film, one can compute the film thickness. The key-remaining issue, is therefore, the detection of the acoustic disturbance once it bounces back from the rear side of the film and reaches the front surface.

Reference is made to the work of investigators at the Brown University in U.S. Pat. No. 4,710,030. The patent states that once a stress pulse is reflected from the rear side of the film and reaches the surface, it changes the optical constants of the surface and near surface. It can be shown that these changes can be as low as a few parts in $10^6$, depending on both the elastic and electronic properties of the film. The change in the optical constants of the surface leads to a change in reflectivity which is detected by monitoring the intensity in a "probe" beam which also illuminates the surface. Given that the change in optical constants is small, the method patented by workers at Brown University, at best, lacks sensitivity.

It is, therefore, desirable to provide improved techniques for film thickness measurements.

SUMMARY OF THE INVENTION

One aspect of the invention is directed towards a system for non-destructively measuring properties of a sample, comprising means for supplying a pump pulse of radiation to a first surface area of the sample to non-destructively generate an elastic pulse in the sample, said elastic pulse causing said first surface area to move; and an interferometer providing an output. The interferometer includes means for providing a pair of a probe pulse and a reference pulse of radiation and for directing the probe pulse to said first surface area when it is moved by the elastic pulse and a reference pulse to a second surface area; and means for interfering the reflections of the pair of pulses.

Another aspect of the invention is directed towards a method for non-destructively measuring properties of a sample, comprising supplying a pump pulse of radiation to a first surface area of the sample to non-destructively generate an elastic pulse in the sample, said elastic pulse causing said first surface area to move; providing a pair of a probe pulse and a reference pulse of radiation; directing the probe pulse to said first surface area when it is moved by the elastic pulse and the reference pulse to a second surface area, and interfering the reflections of the pair of pulses.

BRIEF DESCRIPTION OF THE DRAWINGS

FIG. 1 is a schematic diagram of a system for generating elastic pulse(s) in a sample in an interferometer for detecting the elastic pulse(s) for determining film thickness to illustrate the invention.

FIG. 2 is a schematic diagram of a first embodiment of the system of FIG. 1 in a common path/time differential configuration.

FIGS. 3A and 3B are schematic diagrams of a portion of the embodiment of FIG. 2 illustrating the polarization states of, respectively, the probe pulse and the reference pulse in such portion.

FIG. 4A is a timing diagram of the pump pulse and the pair of probe and reference pulses at different points in the optical path until the pulses reach the sample.

FIG. 4B is a timing diagram of the pump pulse and the pair of reference and probe pulses after reflection from the sample.

FIG. 4C is a timing diagram of the pair of probe and reference pulses upon reaching the detector of FIG. 2.

FIG. 5 is a plot of measured signal output as a function of time of the detector of FIG. 2 in measuring a metal layer of two different thicknesses to illustrate the invention.

FIG. 6 is a schematic diagram of a second embodiment of the system of FIG. 1.

FIG. 7 is a schematic diagram of a third embodiment of the system of FIG. 1. for generating elastic pulse(s) in a sample and an interferometer for detecting the elastic pulse (s) to determine film thickness to illustrate an embodiment of the system of FIG. 1, where such embodiment is slightly different from the embodiment of FIG. 6.

FIG. 8 is a schematic diagram of a fifth embodiment of the system of FIG. 1, where such embodiment is slightly different from the embodiment of FIG. 2.

FIG. 9 is a schematic diagram of a fourth embodiment of the system of FIG. 1.

FIG. 10 is a schematic diagram of another embodiment of the system of FIG. 1 in which the interferometer employs a Wollaston prism.

FIG. 11 is a schematic diagram of another embodiment of the system of FIG. 1, where a lens with a central aperture is employed.

FIG. 12 is a schematic diagram of a system for generating elastic pulse(s) in a sample in an interferometer for detecting the elastic pulse(s) for determining film thickness in an approach different from that of FIG. 1 to illustrate the invention, where the interferometer is of the Michelson type.

For simplicity in description, identical components are labelled by the same numerals in this application.

DETAILED DESCRIPTION OF THE PREFERRED EMBODIMENT

FIG. 1 is a schematic diagram of a system 10 for inducing one or more elastic pulse(s) in a sample, where system 10 includes an interferometer for detecting the elastic pulse(s) to determine the film thickness of the sample and to illustrate a preferred embodiment. As shown in FIG. 1, system 10 includes a laser 12 supplying radiation at an optical frequency, in the form of a beam of periodic sequence of pulses at a first frequency to beamsplitter 14 which diverts a portion of the beam towards a detector 16. Detector 16 detects variations in intensity of the pulses supplied by laser 12 and supplies such information to data acquisition unit and personal computer 18 for comparison with other data so that errors in the data caused by the intensity fluctuations of the laser 12 may be reduced or eliminated. The bulk of the energy supplied by laser 12 passes through beamsplitter 14 and continues to beamsplitter 20 which divides the energy into two portions: a first portion as pump pulses in a pump beam for generating elastic pulses in the sample and a second portion for use in the interferometer 40 to detect the elastic pulse(s) for film thickness measurement of the sample. To simplify the figures, the detector 16 and beam splitter 14 are omitted in figures subsequent to FIG. 1.

Beamsplitter 20 splits the sequence of pulses from laser 12 into two sequences of the same frequency; one being the sequence of pump pulses and the other the sequence of pulses that are converted into a sequence of pairs of reference and probe pulses in the manner described above. The sequence of pump pulses are modulated by an acousto-optic modulator (AOM) or chopper 24 which blocks periodically the passage of the sequence of pump pulses at a modulation frequency, so as to generate a periodic burst of pump pulses at a second frequency equal to the frequency at which the pump pulses are let through the AOM or chopper 24.

Thus, as shown in FIG. 1, the pump pulses are reflected by mirror 22 through an AOM or chopper 24 as a sequence of bursts of pulses and reflected by another mirror 26 towards the sample 30. The pulses are supplied by laser 12 at a first frequency of about 100 MHz. Each pump pulse is absorbed within one absorption length from surface 30a of the sample, giving rise to change in local temperature of the surface and causing the surface to undergo thermal stresses leading to an elastic pulse which propagates down through the sample at the speed of sound in the sample. The elastic pulse is reflected by an interface in the sample between different layers as echoes and such echoes propagate back towards the surface 30a of the sample. The elastic pulse and its echoes cause the surface to move to, for example, new positions 30a' for a short time.

The second portion of the energy supplied by laser 12 is reflected by beamsplitter 20 along a delay path 32 which comprises a retroreflector 34 mounted on a motorized translation stage and mirror 36 to an interferometer 40 which detects the movement of the surface 30a caused by the elastic pulses. The output of the interferometer 40 is provided to a synchronizing means such as a lock-in amplifier 42 which also receives the modulation second frequency from the AOM or chopper 24. Lock-in amplifier 42 amplifies the output of the interferometer at the modulating frequency of AOM or chopper 24 (or a frequency related to such modulating frequency, as described below) and supplies the amplified signal to data acquisition and personal computer unit 18. Delay unit with motor 36 is controlled by motor controller 44 so as to vary a timing relationship between the pulses supplied by interferometer 40 for sampling surface 30a relative to the pump pulses in a manner described in detail below. Data acquisition and personal computer unit 18 is then used to compute film thickness values. While in FIG. 1, the pump beam is shown to be at an oblique angle to surface 30a, it will be understood that this may or may not be the case, depending on the embodiment of system 10, as described in more detail below.

FIG. 2 is a schematic view of one embodiment 10A of the system of FIG. 1 in a common path/time differential configuration. System 10A differs from system 10 of FIG. 1 in that the beam passed by polarizing beamsplitter 20' is used in the interferometer whereas the beam reflected by the polarizing beamsplitter 20' is the pump beam, and in that the varying delay 34' mounted on a motorized translation stage is in the optical path of the pump beam rather than in the path of the beam to the interferometer 40. System 10A also includes an AOM or chopper 52 for modulating at a third frequency the sequence of pulses passed by polarizing beamsplitter 20' to the interferometer, so that pulses are provided to the interferometer in bursts of pulses at the third frequency. The frequencies of modulation of AOM or chopper 52 and AOM or chopper 24 are supplied to lock-in amplifier 42 which amplifies the output of the interferometer 40 at a difference frequency substantially equal to the difference between the second modulation frequency applied by AOM or chopper 24 and that (third frequency) applied by AOM 52 to reduce the effects of noise and then supplies the amplified signal to data acquisition and personal computer unit 18 for detection and analysis. Another feature distinct about system 10A is that the pump pulses and the pulses from the interferometer 40 are both directed towards the sample along the same path that is at substantially normal incidence to surface 30a. Both beams are reflected by mirror 54 and focused by lens 56 to sample 30. AOM or chopper 24 is driven by driver 60 and AOM or chopper 52 is driven by driver 62.

The operation of system 10A of FIG. 2 will now be described by reference to FIGS. 3A and 3B which show a portion of system 10A and the polarization states of the reference and probe pulses in the interferometer and in between the interferometer and the sample. Laser 12 supplies linearly polarized light pulses that are reflected by mirror 72 towards a halfwave plate 74. The halfwave plate 74 rotates the plane of polarization of the laser beam pulses with the result that the S-polarization components of the rotated beam pulses are reflected by polarizing beamsplitter 20' as the pump beam and P-polarization components are passed by the beamsplitter 20' as the beam pulses to be used in the interferometer 40. The pump beam is reflected by mirror 76 towards the varying delay 34', where the delay may comprise a retroreflector 78 mounted onto a motorized stage 80 which moves the retroreflector 78 towards or away from mirrors 76 and 82 in order to vary the delay introduced in the path of the pump beam. The pump beam is reflected by mirrors 76 towards retroreflector 78 towards mirror 82 which reflects the pump beam through the AOM or chopper 24 towards a polarizing beamsplitter 84. The beamsplitter reflects the S-polarized pump beam towards mirror 54 which, in turn, reflects the pump beam through lens 56 to sample 30 to create the elastic pulse(s) in the sample.

As shown in FIGS. 3A and 3B, the S-polarization state of the different (pump, reference and probe) beams is illustrated by a dot surrounded by a circle. The P-polarization of the beams (reference and probe) is indicated in FIGS. 3A and 3B by two parallel lines. After being modulated by AOM or chopper 52, the sequence of pulses that passed the polarizing beamsplitter 20' is passed through a quarterwave plate 86 which causes the beam to be a circularly polarized beam with a P-polarized component and a S-polarized component with a phase shift $\pi/2$ between the two components. Beamsplitter 88 passes a portion of each pulse in the incident beam as a reference pulse and reflects the remainder as a corresponding probe pulse, so that two sequences of reference and probe pulses would emerge.

FIG. 3B illustrates the polarization states of the reference pulses. In reference to FIG. 3B, the circularly polarized reference pulses are reflected by beamsplitter 90 towards the polarizing beamsplitter 84 which passes only the P-polarized components of these pulses. Therefore, the P-polarized components of the sequence of reference pulses are reflected by mirror 54 and focused by lens 56 towards sample 30. In reference to FIG. 2, the varying delay 34' mounted on a motorized translation stage is adjusted so that the P-polarized reference pulse reaches sample 30 before a corresponding pump pulse, so that when the reference pulse reaches sample 30, the surface 38 of the sample is stationary and uneffected by the corresponding pump pulse. The pump pulse corresponding to such reference pulse then reaches sample 30 to create an elastic pulse in the sample, where the elastic pulse causes surface 30a of the sample to move.

The polarization states of the sequence of probe pulses are illustrated in FIG. 3A. The sequence of probe pulses are reflected by beamsplitter 88 and rotated by halfwave plate 92 which causes the phase $\pi/2$ introduced to be associated with the P-polarized components rather than with the S-polarized components as shown in FIG. 3A. Such circularly polarized beam is reflected by mirrors 50 towards beamsplitter 90 to introduce a fixed delay between the probe pulse and its corresponding reference pulse. After passing through beamsplitter 90, the P-polarized component together with the phase $\pi/2$ is passed by polarizing beamsplitter 84, reflected by mirror 54, and focused by lens 56 towards sample 30. The relative timing of the fixed delay introduced by the additional optical path length from beamsplitter 88 to mirrors 50 and then to beamsplitter 90 relative to the delay introduced by the varying delay with delay 34' is such that the probe pulse reaches sample 30 after the corresponding pump pulse has reached sample 30 to create an elastic pulse therein and at a time when surface 30a of the sample is caused to move by the elastic pulse. This permits the probe pulse to detect the movement of surface 30a caused by the elastic pulse.

The pump pulses are partly absorbed by the sample 30 and partly reflected or scattered. However, since the reflections of the pump pulses are S-polarized, they will be reflected by the polarizing beamsplitter 84, which prevents the S-polarized reflections or scattering of the pump pulse from entering the interferometer 40. The return of the reflections of the pump pulses towards laser 12 is prevented by isolator 13.

Reflections of the reference and probe pulses, however, are P-polarized and are passed by polarizing beamsplitter 84 to the interferometer 40. Referring now to FIG. 3B, the reflections of the reference pulses are passed by beamsplitter 90 to mirrors 50 and converted into S-polarized light by halfwave plate 92. Such S-polarized reference pulses are passed by beamsplitter 88 and polarizer 94 before they reach detector 96. Detector 96 is adapted to detect at a difference frequency substantially equal to the difference between the frequencies of AOMs or choppers 24 and 52, or a multiple thereof.

In reference to FIG. 3A, the reflections of the probe pulses are reflected by mirror 54, passed through polarizing beamsplitter 84 while it retains the original polarization state of the probe pulse, namely, P-polarized with phase difference $\pi/2$ relative to the P-polarization. After reflection by beamsplitters 90 and 88, such pulse is passed by polarizer 94 before it reaches detector 96.

From the above description of the reference pulse and the probe pulse, it will be noted that the reference pulse and its reflection and the probe pulse and its reflection travel over the same optical path. Thus, beamsplitter 88 splits the incoming light beam from quarterwave plate 86 into a reference pulse and a probe pulse directly along two different paths towards beamsplitter 90 in the forward direction heading towards the sample. The reference pulse is directed along a first short optical path directly towards beamsplitter 90 as shown in FIG. 3B, while the probe pulse is reflected towards mirrors 50 and then towards beamsplitter 90 along a second path of greater optical length, before both pulses are directed towards polarizing beamsplitter 84, mirror 54 and lens 56 towards the sample. The sample reflects the two pulses and in the reverse traveling directions, the reflection of the reference pulse is directed towards the second longer path of greater optical length involving mirrors 50 and halfwave plate 92 whereas the reflection of the probe pulse is directed along the first path of shorter optical length directly towards beamsplitter 88 as shown in FIG. 3A. Therefore, the total optical path length travelled by the reference pulse and by its reflection from beamsplitter 88 towards the sample and back is substantially the same as the total optical path length travelled by the probe pulse from beamsplitter 88 towards the sample and by its reflection from the sample back to beamsplitter 88. Therefore, the reflections of the two pulses will arrive at beamsplitter 88 at approximately the same time and will start to interfere at polarizer 94.

The polarizer 94 has its optical axis at about 45° to the P- and S-axis so that it passes equal components of the S-polarized reflection of the reference pulse and the P-polarized reflection of the probe pulse towards detector 96 for detecting the interfering signal reflections of the two pulses.

As noted above, the quaterwave plate introduces a phase difference $\pi/2$ between the equal amplitude S and P components. By choosing a quaterwave plate that introduces a 90° or $\pi/2$ phase difference between the two components, it is possible to render the detection of the phase difference between the reference and probe pulses particularly sensitive. Without the phase difference $\pi/2$ that has been introduced, the phase shift that is measured by detector 96 would be proportional to the cosine of the phase difference between the reference and probe pulses. By introducing an additional 90° phase difference between the two pulses, the phase shift detected by detector 96 becomes proportional to the sine of the phase difference, which for small angles is substantially proportional to the phase difference itself.

For a small height change of $\delta z$ of the surface 30a of the sample, the phase shift as experienced by the probe beam relative to the reference beam at normal incidence is $2K\delta z$ where K is $2\pi/\lambda$ is the propagation constant at wavelength $\lambda$. Therefore, once the phase shift is measured, the height or elevation change can be readily calculated.

FIG. 4A is a timing diagram of the pump pulse and a pair of probe and reference pulses propagating in the embodiment 10A of FIG. 2. Each signal that is amplified by lock-in amplifier 42 corresponds to a pump pulse and a pair of reference and probe pulses. The pump pulse and the corresponding pulse from which the corresponding probe and reference pulses are derived overlap in time as shown in FIG. 4A, when the three pulses are on the first polarizing beamsplitter 20'. The pump pulse passes through an optical path which includes a varying delay 34' and reaches the sample at time t=0. As noted above, the delay introduced by varying delay 34' is such as to delay the arrival of the pump pulse to until after the arrival of the corresponding reference pulse as shown in FIG. 4A. Therefore, when the corresponding reference pulse reaches the sample, the surface 30a of the sample is essentially stationary and unaffected by the pump pulse. The fixed delay introduced by the optical path length difference between two optical paths outlined above between the beamsplitter 88 and beamsplitter 90 is such as to delay arrival of the corresponding probe pulse so that it arrives at sample 30 shortly after the arrival of the pump pulse as shown in FIG. 4A. The probe pulse, therefore, arrives at the sample in time to detect movement of sample surface 38 caused by acoustic echoes 81 caused by the pump pulse.

FIG. 4B is a timing diagram illustrating reflections of the pump pulse and of the reference and probe pulses. Since the surface 30a of the sample is substantially stationary, the reflection of the reference pulse may retain its original shape whereas the reflection of the probe pulse is affected by the movement of the sample surface. The reflections of the reference and probe pulses arrive at beamsplitter 88 at substantially the same time to interfere and detected by detector 96 as described above and as shown in FIG. 3C.

FIG. 5 is a graphical plot obtained from an experiment of the phase shift detected between the reference and probe pulses as a function of time as detected from a layer of 96 nm and a layer of 180 nm thick titanium film on a thick substrate of silicon. By changing the varying delay 34', it is possible to detect the position of surface 30a at different times to yield the phase shift curve between the reference and probe pulses shown in FIG. 5. Since the silicon substrate is thick, the reflection from the bottom of the substrate may be ignored. As shown in FIG. 5, for the 96 nm layer, the pump beam causes an acoustic pulse to be generated with high amplitude at about 0 picoseconds from an arbitrary time zero. This acoustic pulse propagates downwards through the titanium film and is reflected by the interface between the film and the silicon substrate underneath. When the reflection reaches the sample surface 30a, it causes the surface to move and is detected as the first echo at about 28 picoseconds from zero. The first echo propagates downwards and is again reflected by the titanium/silicon interface and the echo propagates upwards to reach the sample surface as the second echo and detected at about 60 picoseconds from zero. Thus, the time that it takes the acoustic pulse to travel from the first echo at 28 picoseconds from the air/titanium interface towards the titanium/silicon interface and back towards the titanium/air interface as the second echo took (60-28) picoseconds. If the speed of sound in titanium is known, then the thickness of the titanium film is given by such speed times half of the time interval between the first and second echos as shown in FIG. 5. As noted above, the change in height or elevation of the sample surface 30a is proportional to the phase shift between the reference and probe pulses detected by detector 96. Since the primary interest is to detect the timing interval between the first and second echos (or between the time the pump pulse reach the surface 30a and the first echo), it would be adequate to simply derive the time period between the time of the pump pulse reaching the surface and the first echo or that between the first and second echos from a plot of the phase shift without actually calculating the height change of the surface. As also shown in FIG. 5, for the 180 nm layer, the first echo occurs at about 58 picoseconds, and the same calculation may be made by obtaining the time interval between the pump pulse reaching the surface at time 0 and the first echo (58 picoseconds).

FIG. 6 is a schematic view of a system for generating an elastic pulse in the sample and for detecting the elastic pulse for thickness measurement to illustrate another embodiment of the system of FIG. 1. The embodiment of FIG. 6 differs from that of FIG. 2 only in that the pump pulses are supplied to the sample along paths that are different from the reference and probe pulses, unlike that in FIG. 2. Thus, the position of mirror 82 is placed such that it reflects the pump pulses towards beamsplitter 84 along a path that is offset from the path of the reference and probe pulses, so that the pump pulses and their reflections also travel along paths that are offset from the path of reference and probe pulses and their reflections. When focused by lens 56, the pump pulses travel along a path towards the sample that is at a small angle to the normal direction to the sample. The reflection of the pump pulse is, therefore, also at a small angle to the normal direction to the sample and away from the paths of the reference and probe pulses which travel in a direction substantially normal to the sample surface. The reflection of the pump pulse is directed towards a beam dump 98. The embodiment of FIG. 6 has the advantage that the amount of scattering of the pump pulse reaching the detector 96 is reduced.

FIG. 7 is a schematic view of another embodiment of the system of FIG. 1. The embodiment 10C of FIG. 7 is essentially the same as embodiment 10B of FIG. 6, except that the AOM or chopper 52 is replaced by a frequency doubling crystal 52'. Instead of modulating the reference and probe pulses by periodically blocking the pulses to create pulse bursts, crystal 52' alters the optical frequency of a small portion of the energy of the laser pulses themselves. For example, if the laser wavelength is at 800 nm, then crystal 52' causes the wavelength of the altered portion of the pulses to be at 400 nm, while leaving the remaining unaltered major portion of the energy of the pulses at the wavelength of 800 nm. Harmonic separator 20" passes the altered portion of the laser pulses at the higher frequency to the interferometer 40 to be used for generation of the reference and probe pulses and for detection of displacement of surface 30a as in the embodiment of FIG. 6 and the unaltered energy to the pump beam path for generating elastic pulses in the sample as in the embodiments described above. An isolator 13 has been inserted between the laser 12 and mirror 72 to prevent reflections from the optical components from reaching laser 12 to affect its stability. A notch or other type of filter 99 is also included between beamsplitter 88 and detector 96 to pass radiation at the shorter wavelength caused by crystal 52' and to block radiation at the wavelength of the laser. The lock-in amplifier 42 then amplifies the output of the interferometer 40 at a frequency substantially equal to the second modulation frequency applied by AOM or chopper 24, or a multiple thereof, to reduce the effects of noise and then supplies the amplified signal to data acquisition and personal computer unit 18 for detection and analysis. Detector 96 is adapted to detect at a frequency substantially equal to the frequency of AOM or chopper 24, or a multiple thereof.

FIG. 8 is a schematic view of another embodiment of the system of FIG. 1. System 10D of FIG. 8 is essentially the same as the embodiment 10A of FIG. 2 except that the AOM or chopper 52 of FIG. 2 is replaced by a frequency doubling crystal 52', which operates in the same manner as described above in reference to FIG. 7. An isolator 13 has been inserted between the laser and mirror 72 and a filter 94 has been inserted between beamsplitter 88 and detector 96. The advantages of using a frequency doubling crystal and filter are described above by reference to FIG. 7. The lock-in amplifier 42 then amplifies the output of the interferometer 40 at a frequency substantially equal to the second modulation frequency applied by AOM or chopper 24, or a multiple thereof, to reduce the effects of noise and then supplies the amplified signal to data acquisition and personal computer unit 18 for detection and analysis. Detector 96 is adapted to detect at a frequency substantially equal to the frequency of AOM or chopper 24, or a multiple thereof.

FIG. 9 is a schematic view of yet another embodiment of the system of FIG. 1. The embodiment 10E of FIG. 9 differs from the prior embodiments in that the pump pulses are further spatially separated from the path of the reference and probe pulses in that it is reflected off of a mirror 82' and focused by a lens 56' that are not used to reflect or focus the reference and probe pulses, when the pump pulses are directed to the sample. Thus, as shown in FIG. 9, the pump pulses are reflected by a mirror 82' and focused by lens 56' towards the sample, while the probe and reference pulses are reflected by mirror 82 and focused by lens 56 towards the sample. By spatially further separating the pump pulses from the path of the reference and probe pulses, the amount of scattering of the pump pulses that is detected by the interferometer would be reduced. Furthermore, by using mirror 82' and lens 56' that are separate from the optical elements for reflecting and focusing the reference and probe pulses, the amount of noise caused by scattering in such components that reach the interferometer is further reduced. The arrangement of the first and second optical paths between beamsplitters 88 and 90 are also somewhat different from that of prior embodiments.

FIG. 10 is a schematic view of still another embodiment 10F of the system of FIG. 1. As shown in FIG. 10, the laser pulses, after reflection by beamsplitter 20, modulated by AOM or chopper 24 and reflections from mirrors 76, 82a, 82b, emerge as pump pulses that impinge the sample 30 at a first surface area 30' as shown in FIG. 10. System 10F employs a Wollaston prism instead of a beamsplitter to separate the measuring pulses into reference and probe pulses. Thus, as shown in FIG. 10, the pulses that are passed by beamsplitter 20 and delayed by delay 34 are expanded by beam expander 152, passed by a beamsplitter 154 and are separated by Wollaston prism 156 into two separate beams 160, 162. Lens 164 focuses pulses in beam 162 to the first surface area 30' but focuses pulses in beam 160 towards a second surface area 30" separated from but close to surface area 30'.

The pulses in beam 162 are the probe pulses, the reflections of which would be affected by movement of the surface area 30' of the sample caused by the pump pulses, while the reflections of the reference pulses in beam 160 would not be so affected. Assuming that the surface areas 30' and 30" are close enough so that the surface area 30" can serve as a reference to replace the surface area 30' when it is not moved by the pump pulse, interference of the reflections of the corresponding probe and reference pulses will yield a phase shift to indicate the movement of surface 30" caused by the pump pulse. Lens 164 focuses the reflections of the probe and reference pulses towards the Wollaston prism 166 at the same beam position so that the two pulses will interfere. The two pulses are reflected by beamsplitter 154 towards the polarizing beamsplitter 180, which passes the P-polarized components of the interference signals to detector 172 through lens 176 and reflects the S-polarized components of the interference signals through lens 178 towards a detector 174. The outputs of the detectors may then be used as described above in reference to FIG. 5 to determine film thickness.

From the above, it is evident that instead of directing the reference pulse towards the same area that will be affected by the pump pulse prior to arrival of the pump pulse, the embodiment 10F of FIG. 10 directs the reference pulse to a surface area separated from, but close to, the area impinged by the pump and probe pulses. Furthermore, the reference and probe pulses are supplied to sample 30 substantially at the same time.

FIG. 11 is a schematic view of one more embodiment of the system of FIG. 1. As in the embodiment 10F of FIG. 10, embodiment 10G of FIG. 11 expands spatially the delayed pulses from beamsplitter 20 and supplies the expanded beam towards a beamsplitter 154 which reflects a portion of the beam energy towards a mirror 182; mirror 182 in turn reflects such energy back towards the beamsplitter. The portion of the beam that passes beamsplitter 154 reaches lens 184. Lens 184 has a center portion 184a which is substantially flat or planar which acts as an aperture; aperture 184a passes the center portion of the beam without focusing as a collimated beam 186a towards sample 30 and illuminates a relatively large area 300 of the sample surface. The remaining portion 186b (having a cylindrical cross-section) of the beam is focused by lens 184 towards a small area 30' within the large area 300, where the area 30' is the portion of the sample surface that receives the pump pulses from mirror 82b as in FIG. 10. Upon reflection by sample 30 and collimation by lens 184, reflections of portions 186a, 186b again form an integral reflection beam.

The integral reflection (i.e. reflections of both portions 186a and 186b) from the sample interferes with the reflection of the beam energy from mirror 182 at beamsplitter 154 and the interfering signals are reflected by beamsplitter 154 towards beamsplitter 192. Beamsplitter 192 in turn reflects a portion of such interfering signals to aperture 194 and passes the remaining portion towards aperture 202. Spatial filter or aperture 194 is such that it blocks the passage of the interfering signals which include reflection of the cylindrical portion 186b of the beam. Spatial filter or aperture 202 blocks the passage of the interfering signals which include reflection of signals originating from center portion 186a of the beam.

Signals passed by aperture 194 are focused by lens 196 to detector 198 which detects the interfering signals related to the center portion 186a of the beam which is reflected from the large area 300 of the surface. Such signals indicate the position of the large area 300. Even though the area 300 includes the portion 30' which is affected by the pump pulse, since the area 300 is much larger than area 30' affected by the pump pulse, the signal output of detector 198 would still serve as an adequate reference for the sample surface that is unaffected by the pump pulse. Area 300 may have dimensions of the order of about 100 µm to 1 mm, and area 30' may have dimensions of about 10 µm to 50 µm.

Signals passed by aperture 202 are focused by lens 204 to detector 206 which detects the interfering signals related to the cylindrical portion 186b of the beam which is reflected from the small area 30' of the surface. The interfering signals detected by detector 206 indicates, therefore, movement of portion 30' of the surface caused by the pump pulse. A comparison of the outputs of detectors 198, 206 will yield the phase shift between the reference and pump pulses and, therefore, an indication of the change in position of surface area 30' as caused by the pump pulse.

In the above embodiments, the reference pulses have been directed to the sample surface, either at the same surface area which also receives the pump pulse and probe pulse, or separated from it by a small distance or directed at a larger area that includes the surface area which receives the other two pulses. It will be understood that, however, that this is not necessary, as illustrated in FIG. 12. FIG. 12 is a schematic diagram of a system for generating elastic pulse (s) in a sample and an interferometer for detecting the elastic pulse(s) for determining film thickness in an approach different from that of FIG. 1 to illustrate the invention, where the interferometer is of the Michelson type. As shown in FIG. 12, the embodiment 300 functions in essentially the same manner as the prior embodiments except that some of the energy in pulses from beamsplitter 20 and mirror 36' are reflected towards mirror 304 as reference pulses instead of being directed towards the sample. The remaining energy of the pulses from beamsplitter 20 and mirror 36' is passed by beamsplitter 302 towards the sample as probe pulses for detecting movement of surface 30a of the sample 30 in a manner similar to that of the prior embodiments. The reflection of the probe beam from surface 30a and the reflection of the reference beam from mirror 304 interfere at beam splitter 302. Such interfering signals are detected by detector 306. The detector output may then be used to determine film thickness by means of the method described in reference to FIG. 5.

While the invention has been described by reference to various embodiments, it will be understood that different changes and modifications may be made without departing from the scope of the invention which is to be defined only by the appended claims and their equivalents.

What is claimed is:

1. A system for non-destructively measuring properties of a sample, comprising:
   a first source of pulsed radiation supplying a pump pulse of radiation to a first surface area of the sample to non-destructively generate an elastic pulse in the sample, said elastic pulse causing said surface area to move; and
   an interferometer providing an output, said interferometer including:
   a detector;
   a second source providing a pair of a probe pulse and a reference pulse of radiation so that the probe pulse is directed to said first surface area when it is moved by the elastic pulse and the reference pulse to a second surface area so that the pair is modified by the sample, and so that the probe pulse together with the modified probe pulse substantially share a common optical path with the reference pulse together with the modified reference pulse between the second source and the detector; and
   optics directing the reflections of the pair of pulses to the detector so that the modified pair of pulses interfere at the detector to provide the output.

2. The system of claim 1, said sample having at least one interface under the surface, said system further comprising a delay device altering a time relationship between the pump pulse and the probe pulse in order to sense changes of the sample surface caused by said elastic pulse.

3. The system of claim 2, wherein the system senses changes in elevation of the sample surface.

4. The system of claim 2, further comprising a processor deriving a distance from the at least one interface to the sample surface from said changes of the sample surface caused by said elastic pulse.

5. The system of claim 2, said delay device including a varying optical delay.

6. The system of claim 1, said first source supplying a sequence of said pump pulses at a first frequency, said second source providing and directing at said frequency a sequence of pairs of said probe and reference pulses to the sample, each pair of said probe and reference pulses corresponding to each of at least some of the pump pulses, wherein each of said modified pairs of said probe and reference pulses interfere to provide output signals.

7. The system of claim 1, further comprising a first modulator modulating the sequence of pump pulses so that the pump pulses are supplied in intermittent bursts at a second frequency before the pump pulses reach the sample, said detector detecting the interferometer output at a frequency related to said second frequency.

8. The system of claim 7, said detector detecting the interferometer output at a frequency substantially equal to the second frequency.

9. The system of claim 7, further comprising a second modulator modulating the sequence of pairs of pulses so that the pairs are supplied in bursts at a third frequency before the pairs of pulses reach the first and second surface areas.

10. The system of claim 9, said second modulator including an acousto-optic modulator or chopper for modulating the sequence of pairs of pulses.

11. The system of claim 10, said detector including a synchronous detector or a lock-in amplifier.

12. The system of claim 9, said detector detecting the interferometer output at a frequency substantially equal to a difference frequency given by the difference between the second and third frequencies, or a multiple thereof.

13. The system of claim 7, said first modulator including a chopper or an acousto-optic modulator for modulating the pump pulse.

14. The system of claim 1, said first source providing radiation pulses of an optical frequency suitable for use as the pump pulses, and said second source including a frequency doubling crystal deriving said pair of probe and reference pulses from said radiation pulses.

15. The system of claim 14, said system further comprising a filter reducing signal components at such optical frequency from the said modified pair of pulses before detection.

16. The system of claim 1, said interferometer including:
   a first beam splitter splitting an input pulse into a probe pulse and a reference pulse;
   a second beam splitter; and
   a first and a second optical path between the two beamsplitters, the second optical path having a path length longer than that of the first optical path, directions of propagation from the first beam splitter toward the second beam splitter along the two optical paths being the forward directions and the directions opposite thereto the reverse directions;
   the second beam splitter being such that the reference and probe pulses propagate along the first and second optical paths respectively in the forward directions so that the reference pulse reaches the sample before the probe pulse.

17. The system of claim 16, wherein the second beam splitter causes the modified reference and probe pulses to travel along the second and first optical paths respectively in the reverse directions, so that the total optical path length traveled by the reference pulse and the modified reference pulse from the sample is substantially the same as the total optical path length traveled by the probe pulses and the modified probe pulse from the sample.

18. The system of claim 16, wherein the second beam splitter reflects the reference pulse towards the first optical path in a forward direction and passes the modified reference pulse from the sample towards the second optical path in a reverse direction.

19. The system of claim 16, said second optical path including a wave plate.

20. The system of claim 1, said interferometer including a birefringent element for splitting an input pulse into the pair of reference and probe pulses, wherein said second surface area is on the sample, and is separated from but near the first surface area.

21. The system of claim 20, said element being a Wollaston prism.

22. The system of claim 1, said interfering means interfering the modified probe pulse with a first pulse and the modified reference pulse with a second pulse.

23. The system of claim 1, said interferometer including a lens defining an optical aperture therein, said lens passing a center portion of an input radiation beam as a core beam towards the second surface, and focusing a cylindrical portion of the input beam to said first surface area, said second area enclosing said first area.

24. The system of claim 1, wherein said second surface is a reference mirror.

25. The system of claim 1, wherein the second surface area is an area of the sample at or near said first surface area.

26. The system of claim 25, wherein said first source directs the pump pulse at an angle from a normal direction to a surface of the sample, and the second source directs the pair of pulses substantially along a normal direction to the sample.

27. The system of claim 1, wherein the sources direct the pump pulse and the pair of pulses along a path or paths substantially normal to a surface of the sample.

28. The system of claim 25, wherein said second surface area includes an area adjacent to the first area substantially unaffected by said elastic pulse.

29. The system of claim 28, wherein said second source directs said pair of pulses substantially simultaneously to said sample.

30. The system of claim 25, wherein said second surface area also includes said first surface area.

31. The system of claim 25, wherein said first and second surface area are substantially the same.

32. The system of claim 25, wherein said second source directs the two pulses in said pair at different times to said sample.

33. The system of claim 25, wherein said first source supplies the pump pulse along a path towards the sample that is spatially separated from a path of the pair of pulses towards the sample.

34. The system of claim 33, wherein said first source includes a first mirror and a first lens reflecting and focusing the pump pulse towards the sample, wherein said second source includes a second mirror and a second lens different from the first mirror and first lens, said second mirror and second lens reflecting and focusing the pair of pulses towards the sample.

35. A method for non-destructively measuring properties of a sample, comprising:
supplying a pump pulse of radiation to a first surface area of the sample to non-destructively generate an elastic pulse in the sample, said elastic pulse causing said surface area to move;
providing a pair of a probe pulse and a reference pulse of radiation;
directing the probe pulse to said first surface area when it is moved by the elastic pulse and the reference pulse to a second surface area so that the pair is modified by the sample, and so that the probe pulse together with the modified probe pulse substantially share a common optical path with the reference pulse together with the modified reference pulse; and
interfering the pair of modified pulses to provide an output.

36. The method of claim 35, said sample having at least one interface under the surface, said method further comprising altering a time relationship between the pump pulse and the probe pulse in order to sense changes of the sample surface caused by said elastic pulse.

37. The method of claim 36, wherein the changes of the sample surface sensed are elevation changes.

38. The method of claim 36, further comprising deriving a distance from said at least one interface to the sample surface from said changes of the sample surface caused by said elastic pulse.

39. The method of claim 36, wherein said altering alters an optical length of an optical delay path.

40. The method of claim 35, wherein said supplying supplies a sequence of said pump pulses at a first frequency, wherein said providing and directing provides and directs at said frequency a sequence of pairs of said probe and reference pulses to the sample, each pair corresponding to each of at least some of the pump pulses, wherein said interfering interferes the modified probe and reference pulses.

41. The method of claim 40, further comprising modulating the sequence of pump pulses so that the pump pulses are supplied in intermittent bursts at a second frequency before the pump pulses reach the sample, and detecting the output at a frequency related to said second frequency.

42. The method of claim 41, wherein said detecting detects at a frequency substantially equal to the second frequency, or a multiple thereof.

43. The method of claim 41, further comprising modulating the sequence of pairs of pulses so that the pairs are supplied in bursts at a third frequency before the pairs of pulses reach the sample.

44. The method of claim 43, wherein said detecting detects at a difference frequency substantially equal to the difference between the second and third frequencies, or a multiple thereof.

45. The method of claim 35, wherein the second surface area is an area of the sample at or near said first surface area.

46. The method of claim 45, wherein said providing and directing directs the pump pulse at an angle from a normal direction to a surface of the sample, and directs the pair of pulses substantially along a normal direction to the sample.

47. The method of claim 45, wherein said providing and directing directs the pump pulse and the pair of pulses along a path or paths substantially normal to a surface of the sample.

48. The method of claim 45, wherein said providing and directing directs the pair of pulses so that said second surface area includes an area adjacent to the first area substantially unaffected by said elastic pulse.

49. The method of claim 48, wherein said providing and directing directs said pair of pulses substantially simultaneously to said sample.

50. The method of claim 45, wherein said providing and directing directs the pair of pulses so that said second surface area also includes said first surface area.

51. The method of claim 45, wherein said providing and directing directs the pair of pulses to the same area.

52. The method of claim 45, wherein said providing and directing directs the two pulses in said pair at different times to said sample.

53. The method of claim 3, wherein said providing and directing directs the reference pulses to a reference mirror in an interferometer.

54. A system for non-destructively measuring properties of a sample, comprising:
   a source of pulsed radiation supplying a pump pulse of radiation to a first surface area of the sample to non-destructively generate an elastic pulse in the sample, said elastic pulse causing said surface area to move; and
   an interferometer providing an output, said interferometer including:
   a detector;
   an optical device deriving from pulsed radiation from the source a pair of a probe pulse and a reference pulse of radiation so that the probe pulse is directed to said first surface area when it is moved by the elastic pulse and the reference pulse to a second surface area and so that the pair is modified by the sample; and
   optics directing the modified pair of pulses to the detector so that the modified pair of pulses interfere at the detector to provide the output, said sample having at least one interface under the surface, said system further comprising a delay device altering a time relationship between the pump pulse and the probe pulse in order to sense changes of the sample surface caused by said elastic pulse.

55. The system of claim 54, wherein the system senses changes in elevation of the sample surface.

56. The system of claim 54, further comprising a processor deriving a distance from the at least one interface to the sample surface from said changes of the sample surface caused by said elastic pulse.

57. The system of claim 54, said delay device including a varying optical delay.

58. The system of claim 54, said source supplying a sequence of said pump pulses at a first frequency, said optical device providing at said frequency a sequence of pairs of said probe and reference pulses to the sample, each pair of said probe and reference pulses corresponding to each of at least some of the pump pulses, wherein each of said modified pairs of said probe and reference pulses interfere to provide output signals.

59. A system for non-destructively measuring properties of a sample, comprising:
   a source of pulsed radiation supplying a pump pulse of radiation to a first surface area of the sample to non-destructively generate an elastic pulse in the sample, said elastic pulse causing said surface area to move; and
   an interferometer providing an output, said interferometer including:
   a detector;
   an optical device deriving from pulsed radiation from the source a pair of a probe pulse and a reference pulse of radiation so that the probe pulse is directed to said first surface area when it is moved by the elastic pulse and the reference pulse to a second surface area and so that the pair is modified by the sample; and
   optics directing the modified pair of pulses to the detector so that the modified pair of pulses interfere at the detector to provide the output, said system further comprising a first modulator modulating the sequence of pump pulses so that the pump pulses are supplied in intermittent bursts at a second frequency before the pump pulses reach the sample, said detector detecting the interferometer output at a frequency related to said second frequency.

60. The system of claim 59, said detector detecting the interferometer output at a frequency substantially equal to the second frequency.

61. The system of claim 59, further comprising a second modulator modulating the sequence of pairs of pulses so that the pairs are supplied in bursts at a third frequency before the pairs of pulses reach the first and second surface areas.

62. The system of claim 61, said second modulator including an acousto-optic modulator or chopper for modulating the sequence of pairs of pulses.

63. The system of claim 62, said detector including a synchronous detector or a lock-in amplifier.

64. The system of claim 59, said detector detecting the interferometer output at a frequency substantially equal to a difference frequency given by the difference between the second and third frequencies, or a multiple thereof.

65. The system of claim 59, said first modulator including a chopper or an acousto-optic modulator for modulating the pump pulse.

66. The system of claim 59, said source providing radiation pulses of an optical frequency suitable for use as the pump pulses, and said optical device including a frequency doubling crystal deriving said pair of probe and reference pulses from said radiation pulses.

67. The system of claim 54, wherein the probe pulse together with the modified probe pulse substantially share a common optical path with the reference pulse together with the modified reference pulse between the optical device and the detector.

68. A method for non-destructively measuring properties of a sample, comprising:
   supplying a pump pulse of radiation to a first surface area of the sample to non-destructively generate an elastic pulse in the sample, said elastic pulse causing said surface area to move;
   providing a pair of a probe pulse and a reference pulse of radiation, wherein said pump pulse and said pair of pulses are derived from a radiation pulse;
   directing the probe pulse to said first surface area when it is moved by the elastic pulse and the reference pulse to a second surface area so that the pair of pulses are modified by the sample; and
   interfering the pair of modified pulses to provide an output, said sample having at least one interface under the surface, said method further comprising altering a time relationship between the pump pulse and the probe pulse in order to sense changes of the sample surface caused by said elastic pulse.

69. The method of claim 68, wherein the changes of the sample surface sensed are elevation changes.

70. The method of claim 69, further comprising deriving a distance from said at least one interface to the sample surface from said changes of the sample surface caused by said elastic pulse.

71. The method of claim 68, wherein said altering alters an optical length of an optical delay path.

72. The method of claim 68, wherein said supplying supplies a sequence of said pump pulses at a first frequency, wherein said providing and directing provides and directs at said frequency a sequence of pairs of said probe and reference pulses to the sample, each pair corresponding to each of at least some of the pump pulses, wherein said interfering interferes the modified probe and reference pulses.

73. The method of claim 72, further comprising modulating the sequence of pump pulses so that the pump pulses are supplied in intermittent bursts at a second frequency before the pump pulses reach the sample, and detecting the output at a frequency related to said second frequency.

74. The method of claim 73, wherein said detecting detects at a frequency substantially equal to the second frequency, or a multiple thereof.

75. The method of claim 73, further comprising modulating the sequence of pairs of pulses so that the pairs are supplied in bursts at a third frequency before the pairs of pulses reach the sample.

76. The method of claim 75, wherein said detecting detects at a difference frequency substantially equal to the difference between the second and third frequencies, or a multiple thereof.

77. The method of claim 68, wherein the second surface area is an area of the sample at or near said first surface area.

78. The method of claim 77, wherein said providing and directing directs the pump pulse at an angle from a normal direction to a surface of the sample, and directs the pair of pulses substantially along a normal direction to the sample.

79. The method of claim 77, wherein said providing and directing directs the pump pulse and the pair of pulses along a path or paths substantially normal to a surface of the sample.

80. The method of claim 77, wherein said providing and directing directs the pair of pulses so that said second surface area includes an area adjacent to the first area substantially unaffected by said elastic pulse.

81. The method of claim 80, wherein said providing and directing directs said pair of pulses substantially simultaneously to said sample.

82. The method of claim 77, wherein said providing and directing directs the pair of pulses so that said second surface area also includes said first surface area.

83. The method of claim 77, wherein said providing and directing directs the pair of pulses to the same area.

84. The method of claim 77, wherein said providing and directing directs the two pulses in said pair at different times to said sample.

85. The method of claim 77, wherein said providing and directing directs the reference pulses to a reference mirror in an interferometer.

86. A system for non-destructively measuring properties of a sample having a surface and at least one interface under the surface, comprising:
a first source of pulsed radiation supplying a pump pulse of radiation to a first surface area of the sample to non-destructively generate an elastic pulse in the sample, said elastic pulse causing said surface area to move; and
an interferometer providing an output, said interferometer including:
a detector;
a second source providing a pair of a probe pulse and a reference pulse of radiation so that the probe pulse is directed to said first surface area when it is moved by the elastic pulse and the reference pulse to a second surface area so that the pair is modified by the sample;
optics directing the reflections of the pair of pulses to the detector so that the modified pair of pulses interfere at the detector to provide the output; and a delay device altering a time relationship between the pump pulse and the probe pulse so that the output indicates changes of the sample surface caused by an echo of said elastic pulse and so that the probe pulse together with the modified probe pulse substantially share a common optical path with the reference pulse together with the modified reference pulse between the second source and the detector.

87. The system of claim 86, wherein the system senses changes in elevation of the sample surface.

88. The system of claim 86, further comprising a processor deriving a distance from the at least one interface to the sample surface from said changes of the sample surface caused by an echo of said elastic pulse.

89. The system of claim 86, said delay device including a varying optical delay.

90. The system of claim 86, said source supplying a sequence of said pump pulses at a first frequency, said optical device providing at said frequency a sequence of pairs of said probe and reference pulses to the sample, each pair of said probe and reference pulses corresponding to each of at least some of the pump pulses, wherein each of said modified pairs of said probe and reference pulses interfere to provide output signals.

91. The system of claim 86, further comprising a first modulator modulating the sequence of pump pulses so that the pump pulses are supplied in intermittent bursts at a second frequency before the pump pulses reach the sample, said detector detecting the interferometer output at a frequency related to said second frequency.

92. The system of claim 91, said detector detecting the interferometer output at a frequency substantially equal to the second frequency.

93. The system of claim 91, further comprising a second modulator modulating the sequence of pairs of pulses so that the pairs are supplied in bursts at a third frequency before the pairs of pulses reach the first and second surface areas.

94. The system of claim 93, said second modulator including an acousto-optic modulator or chopper for modulating the sequence of pairs of pulses.

95. The system of claim 94, said detector including a synchronous detector or a lock-in amplifier.

96. The system of claim 91, said detector detecting the interferometer output at a frequency substantially equal to a difference frequency given by the difference between the second and third frequencies, or a multiple thereof.

97. The system of claim 91, said first modulator including a chopper or an acousto-optic modulator for modulating the pump pulse.

98. The system of claim 86, wherein the probe pulse together with the modified probe pulse substantially share a common optical path with the reference pulse together with the modified reference pulse between the optical device and the detector.

99. A method for non-destructively measuring properties of a sample, said sample having a surface and at least one interface under the surface, comprising: supplying a pump pulse of radiation to a first surface area of the sample to non-destructively generate an elastic pulse in the sample, said elastic pulse causing said surface area to move;
providing a pair of a probe pulse and a reference pulse of radiation;
directing the probe pulse to said first surface area when it is moved by the elastic pulse and the reference pulse to a second surface area so that the pair of pulses are modified by the sample;
interfering the pair of modified pulses to provide an output; and altering a time relationship between the pump pulse and the probe pulse so that the output signal indicates changes of the sample surface caused by an echo of said elastic pulse.

100. The method of claim 99, wherein the changes of the sample surface sensed are elevation changes.

101. The method of claim 100, further comprising deriving a distance from said at least one interface to the sample surface from said changes of the sample surface caused by said elastic pulse.

102. The method of claim 99, wherein said altering alters an optical length of an optical delay path.

103. The method of claim 99, wherein said supplying supplies a sequence of said pump pulses at a first frequency, wherein said providing and directing provides and directs at said frequency a sequence of pairs of said probe and reference pulses to the sample, each pair corresponding to each of at least some of the pump pulses, wherein said interfering interferes the modified probe and reference pulses.

104. The method of claim 103, further comprising modulating the sequence of pump pulses so that the pump pulses are supplied in intermittent bursts at a second frequency before the pump pulses reach the sample, and detecting the output at a frequency related to said second frequency.

105. The method of claim 104, wherein said detecting detects at a frequency substantially equal to the second frequency, or a multiple thereof.

106. The method of claim 104, further comprising modulating the sequence of pairs of pulses so that the pairs are supplied in bursts at a third frequency before the pairs of pulses reach the sample.

107. The method of claim 106, wherein said detecting detects at a difference frequency substantially equal to the difference between the second and third frequencies, or a multiple thereof.

108. The method of claim 99, wherein the second surface area is an area of the sample at or near said first surface area.

109. The method of claim 108, wherein said providing and directing directs the pump pulse at an angle from a normal direction to a surface of the sample, and directs the pair of pulses substantially along a normal direction to the sample.

110. The method of claim 108, wherein said providing and directing directs the pump pulse and the pair of pulses along a path or paths substantially normal to a surface of the sample.

111. The method of claim 108, wherein said providing and directing directs the pair of pulses so that said second surface area includes an area adjacent to the first area substantially unaffected by said elastic pulse or includes the first area.

112. The method of claim 99, wherein said providing and directing directs the reference pulses to a reference mirror in an interferometer.

113. A system for non-destructively measuring properties of a sample, comprising:

means for supplying a pump pulse of radiation to a first surface area of the sample to non-destructively generate an elastic pulse in the sample, said elastic pulse causing said surface area to move; and an interferometer providing an output, said interferometer including:

a detector;

means for providing a pair of a probe pulse and a reference pulse of radiation and for directing the probe pulse to said first surface area when it is moved by the elastic pulse and the reference pulse to a second surface area so that the pair is modified by the sample, and so that the probe pulse together with the modified probe pulse substantially share a common optical path with the reference pulse together with the modified reference pulse between the second source and the detector; and means for interfering the reflections of the pair of pulses to the detector so that the modified pair of pulses interfere at the detector to provide the output.

114. A system for non-destructively measuring properties of a sample having a surface and at least one interface under the surface, comprising:

pulsed radiation means for supplying a pump pulse of radiation to a first surface area of the sample to non-destructively generate an elastic pulse in the sample, said elastic pulse causing said surface area to move; and an interferometer providing an output, said interferometer including:

a detector;

means for providing a pair of a probe pulse and a reference pulse of radiation so that the probe pulse is directed to said first surface area when it is moved by the elastic pulse and the reference pulse to a second surface area so that the pair is modified by the sample;

means for directing the reflections of the pair of pulses to the detector so that the modified pair of pulses interfere at the detector to provide the output; and delay means altering a time relationship between the pump pulse and the probe pulse so that the output indicates changes of the sample surface caused by an echo of said elastic pulse and so that the probe pulse together with the modified probe pulse substantially share a common optical path with the reference pulse together with the modified reference pulse between the second source and the detector.

* * * * *